(12) United States Patent
Niedermeier et al.

(10) Patent No.: US 10,161,880 B2
(45) Date of Patent: *Dec. 25, 2018

(54) TEST CONTAINER FOR TESTING INSPECTION DEVICES

(71) Applicant: KRONES AG, Neutraubling (DE)

(72) Inventors: Anton Niedermeier, Offenstetten (DE); Peter Lindner, Langquaid (DE)

(73) Assignee: KRONES AG (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/388,450

(22) Filed: Dec. 22, 2016

(65) Prior Publication Data

US 2017/0102340 A1 Apr. 13, 2017

Related U.S. Application Data

(63) Continuation of application No. 14/784,301, filed as application No. PCT/EP2014/057716 on Apr. 16, 2014, now Pat. No. 9,557,275.

(30) Foreign Application Priority Data

Apr. 19, 2013 (DE) ........................ 10 2013 103 992

(51) Int. Cl.
  *G01N 21/90* (2006.01)
  *G01N 21/93* (2006.01)
  *B07C 5/34* (2006.01)
(52) U.S. Cl.
  CPC ........... *G01N 21/93* (2013.01); *B07C 5/3408* (2013.01); *G01N 21/90* (2013.01); *G01N 21/9027* (2013.01)
(58) Field of Classification Search
  CPC .... G01N 21/93; G01N 21/90; G01N 21/9027; B07C 5/3408
  (Continued)

(56) References Cited

U.S. PATENT DOCUMENTS 4,664,525 A 5/1987 Tagaya
5,523,560 A * 6/1996 Manique ............ G01N 21/9027
                                                           209/526
(Continued)

FOREIGN PATENT DOCUMENTS

CN 101287981 A 10/2008
CN 101988906 A 3/2011
(Continued)

OTHER PUBLICATIONS

Chinese Office Action dated Dec. 21, 2016; Chinese Patent Application No. 2014800219214; 12 pgs.
(Continued)

*Primary Examiner* — Hoa Pham
(74) *Attorney, Agent, or Firm* — Schmeiser, Olsen & Watts, LLP

(57) ABSTRACT

A test container for checking container inspection machines, which inspection machines are suitable for examining at least a first category of containers for the presence of foreign bodies, with a main body in which a liquid is disposed, with a mouth via which the liquid is able to be introduced into the container, with a first closure by which the container is closed, wherein a foreign body which can be detected by the inspection machine is disposed in the container is provided. The container and/or the liquid disposed therein has a further substance or for example a transmitting device which can be detected by a user and/or by a detection device in order thus to distinguish the test container per se from another container of the category to be inspected.

15 Claims, 1 Drawing Sheet

(58) Field of Classification Search
    USPC .................... 356/426–428, 240.1; 250/223 B
    See application file for complete search history.

(56) References Cited

U.S. PATENT DOCUMENTS

| | | | |
|---|---|---|---|
| 9,557,275 B2* | 1/2017 | Niedermeier | B07C 5/3408 |
| 2005/0221406 A1* | 10/2005 | Arbab | C12Q 1/26 |
| | | | 435/7.92 |
| 2008/0230720 A1 | 9/2008 | Nielson | |
| 2010/0032437 A1 | 2/2010 | Lossau | |
| 2013/0271755 A1 | 10/2013 | Lindner | |
| 2016/0033541 A1* | 2/2016 | Darmstadt | G01N 35/00693 |
| | | | 73/1.02 |

FOREIGN PATENT DOCUMENTS

| | | |
|---|---|---|
| DE | 196 02 655 A1 | 7/1997 |
| DE | 299 10 452 U1 | 8/1999 |
| DE | 199 46 080 A1 | 5/2000 |
| DE | 102011084453 A1 | 4/2013 |
| EP | 0 043 330 A1 | 1/1982 |
| EP | 1083519 A2 | 3/2001 |
| EP | 2392906 A1 | 12/2011 |
| EP | 2581732 A1 | 4/2013 |

OTHER PUBLICATIONS

Notice of Allowance for U.S. Appl. No. 14/784,301, dated Sep. 21, 2016.
International Search Report for PCT Application No. PCT/EP2014/057716, dated Aug. 5, 2014.

* cited by examiner

TEST CONTAINER FOR TESTING INSPECTION DEVICES

CROSS-REFERENCE TO RELATED APPLICATIONS

This application is a continuation application of U.S. application Ser. No. 14/784,301, filed on Oct. 14, 2015, which claims priority to PCT Application No. PCT/EP2014/057716, having a filing date of Apr. 16, 2014, based on DE 10 2013 103 992.8, having a filing date of Apr. 19, 2013, the entire contents of which are hereby incorporated by reference.

FIELD OF TECHNOLOGY

The following relates to a container and in particular a test container for testing inspection plants.

BACKGROUND

It is often necessary to examine manufactured and in particular filled containers for specific defects, for example for the presence of shards of glass within the container or for the presence of contaminants. For this purpose the containers to be examined run through these inspection devices and it is ascertained whether specific defects are present. However, it is also necessary to examine the precision of such inspection plants. For this purpose original containers are used and they are provided with a test contaminant. If the inspection device recognises this container, it may be assumed that the inspection device is working properly. However, the problem of such containers is that the containers wear relatively quickly, since the product located therein is contaminated with germs. These can multiply phenomenally in most beverages and thus make the test container unusable. If unfilled containers are used, the test results are often less significant, above all because the index of refraction of the liquid essentially necessitates different optical arrangements than empty containers.

Furthermore in the past the outputs are permanently increased and so also the throughput of containers per unit of time. If the test containers are filled with a product which is particularly attractive for consumption, such as for example alcoholic beverages and other premium products, there is a danger that such a test container will pass through the inspection device and will no longer be recognised later.

SUMMARY

Therefore an aspect of embodiments of the invention are to ensure that for safety reasons the container is not opened in error and the content consumed. This is important in particular because the product may be spoiled or, much worse, may include test contamination. This test contamination may be for example rubber parts, but may also be glass or steel beads or glass fragments. In addition for the detection of suspended material cellophane or the like is sometimes also introduced into the containers. The size of these introduced solid bodies is for example 5×5×5 mm down to 1×1×1 mm or also 3.0×0.5 mm in the case of glass fragments. However, these products can be very harmful when consumed by people.

Therefore an aspect is to avoid accidental consumption of the contents of such test containers by the user.

A test container according to embodiments of the invention for examining inspection machines for testing containers or container inspection machines respectively, wherein these inspection machines are adapted to examine at least a first category of containers for the presence of foreign bodies, has a main body in which a liquid is disposed. Furthermore the test container has a mouth by means of which the liquid can be introduced into the container, as well as a first closure by means of which the container is closed. In this case a foreign body which can be detected in particular optically by the inspection machine is disposed in the container.

According to embodiments of the invention the container and/or the liquid disposed therein has a detection means or test element to be detected 40 which can be detected by a user and/or a detection device in order thus to distinguish the test container per se from another container of the category to be inspected.

Therefore a test container is proposed which even at high production speeds prevents the test container from being opened later by a user and in particular prevents consumption of the content thereof. In this case it is on the one hand conceivable that the detection means or test element to be detected 40 can be detected by a machine which in particular is disposed downstream of the inspection machine, but it is also possible on the other hand that the liquid itself is recognised by a user, in particular already before consumption, as not suitable for consumption.

Advantageously the container is a container which is at least partially transparent, for example a glass bottle or a plastic bottle, which is at least partially transparent for light, in particular light in the visible wavelength range. The liquid is advantageously also a liquid which is at least partially transparent for light in the visible wavelength range.

In a further advantageous embodiment a further substance is located in the liquid, making it possible to differentiate the container on the basis of a taste and/or a smell and in particular a smell of the liquid. In the prior art it can happen that in the event of a malfunction of the full bottle inspection test bottles enter a labelling machine where they are equipped as a saleable product. Thus it may happen for example that labels are superimposed on any test container markings which may be present on the container and thus the explosive nature of the content is no longer obvious to anyone.

In a further advantageous embodiment the further substance is selected from a group of substances containing acetone, raw pyridine, crystal violet, fusel oil, isopropyl alcohol, methyl ethyl ketone, methyl isopropyl ketone, ethyl sec-amyl ketone, wood alcohol, rock oil, methanol, thiophene, mixtures or compositions consisting of these substances and the like. In particular isopropyl alcohol has proved particularly suitable for the said liquid. In this embodiment it is possible that, if a container has actually run through the complete system and thus has even been labelled, this container can still be recognised very quickly by a user from the smell without the user consuming the liquid located in the container. Thus in this embodiment a denaturing of the liquid is advantageously carried out.

In a further advantageous embodiment several foreign bodies with physical characteristics which differ from one another are disposed in the container. In this case these foreign bodies can differ in particular with regard to their colour, their density, their flexibility, their size, etc. In this way several characteristics of the machines can be tested. Thus, for example, it is possible to test whether a foreign body lying on the floor of the container is detected, it is possible to test whether a foreign body is detected which is more easily swirled up in the context of a movement of the container, and foreign bodies of different colours can be checked.

In a further advantageous embodiment at least one foreign body is fixed relative to the container. Thus it would be possible that this foreign body is adhered to the inner wall of a base of the container or also to a side wall of the container. In this way the precise location of a foreign body in the container can be precisely defined during the inspection.

In a further advantageous embodiment the test container has an identification element which is detectable by a machine. As mentioned above, after labelling a test container which has been lost can in some circumstances be found only with substantial effort. At filling rates of 1,100 containers per minute, within a few minutes of production a search effort of several hours is produced. It is therefore proposed here to equip the test container with an identification element which is capable of transmitting to a receiving device the information that this container is a test container. Thus this identification element can advantageously also transmit the type of contamination in order thus for example in a subsequent machine, such as a labelling machine, to be identified as "not belonging there". Consequently it would be possible to remove this container again.

Thus it would be possible for example for this identification element to be detected by means of an initiator, but on the other hand it may also serve as a control element in order in particular to serve in any machine after the inspection machine as a control element for discharging. Thus for example a special test bottle sensor in a labelling machine can recognise an incoming test container as such. This may be eliminated or a machine stoppage may be initiated. The same could also be effected in subsequent machines, such as for instance a packaging machine. This identification element is preferably a transmission element, such as for example a RFID tag or the like. However it would also be possible for an inspection to be carried out by means of an optically perceptible means, for example a different colour of a container closure.

In a further advantageous embodiment the container has a second closure which closes the container in addition to the first closure. Thus in the prior art the problem arises that when test containers pass through an inspection unit several times the closures of the containers are loosened for example by the centring bells. In this case a gas or also the product can escape. It is therefore proposed that in addition to the above-mentioned first closure a second closure element is disposed in particular in the container. Advantageously in this case both closures are suitable for closing the container so that the second closure per se is redundant. This second closure constitutes a further safety means in order to prevent the product from escaping from the container and in order also to prevent a user from consuming the content of the container. In this case this second closure can also have the above-mentioned identification means. The first closure is in particular a closure which lies at least in sections in contact on an outer wall of the container, such as for instance a screw cap, which is screwed onto an external thread disposed on the container or for instance a crown cap.

The second closure is advantageously disposed within a mouth region of the test container. In this case the closure may for example be a grippable closure element which is disposed in the bottle neck. Thus for example the closure may be a rubber element which is anchored firmly in the container neck by means of gripping via two pressure plates. Thus the identification element could also be installed in this relatively large element. It would also be possible for test objects to be disposed in a defined manner on this second closure element. Thus it would for example be conceivable for a test object also to be disposed on this closure element by means of an (in particular transparent) rod member, in order thus to dispose this element within the liquid at a defined position.

In a further advantageous embodiment the liquid in the container has at least one substance with a germ-killing action. Basically in such test conditions it is attempted to use or to create a filling medium which is similar in appearance and index of refraction to the product actually used. However, it is proposed here at least also to use a liquid which prevents the multiplication of germs for a relatively long period of time. Thus for example as a replacement for beer a denatured, coloured, high-percentage alcohol solution could be used. In addition it would also be conceivable for the container, which has been prepared with the test contamination, filled and closed, to be subjected to a treatment until all germs capable of multiplying are deactivated.

Thus the test container is preferably a test container which is produced (and preferably also filled) at least partially under sterile conditions. Thus for example the test container itself may have been produced under sterile conditions, but it would also be possible that the liquid in the container has been introduced under sterile conditions and/or also the closure of the container has been manufactured and attached to the container under sterile conditions.

In this way sterility and thus also a longer shelf life can be achieved. This treatment may for example be a heat treatment or a simple heating respectively to just below the boiling point for a few hours, which effectively slows down the multiplication of germs. Also another type of radiation which penetrates into the medium used for disinfection or for sterilisation is conceivable, such as for example UV light or also electron irradiation. In addition, as mentioned above, the test containers themselves are also produced under clean conditions, and, as mentioned, sterile liquid, germ-free test contamination (such as rubber, shards of glass and steel beads), mould-resistant glues etc. can be used.

The test container is advantageously a plastic container or a glass container. Thus, however, the glass itself can be treated before the introduction of the liquid. Thus for example the glass body could have been roughened or made rough or also the in particular inner wall of the container could have been treated by means of etching, lasers or also by inclusions in glass or thermal action.

In a further advantageous embodiment the containers can also be provided with features such as for example a two-dimensional or transponder coding or also a coding which gives information about the defect totals or defect locations to be achieved.

Overall as a result a test container is made available, which on the one hand is reliable in handling but on the other hand can also be used over a longer time period.

BRIEF DESCRIPTION

Some of the embodiments will be described in detail, with reference to the following figures, wherein like designations denote like members, wherein.

DETAILED DESCRIPTION

Figure 1:
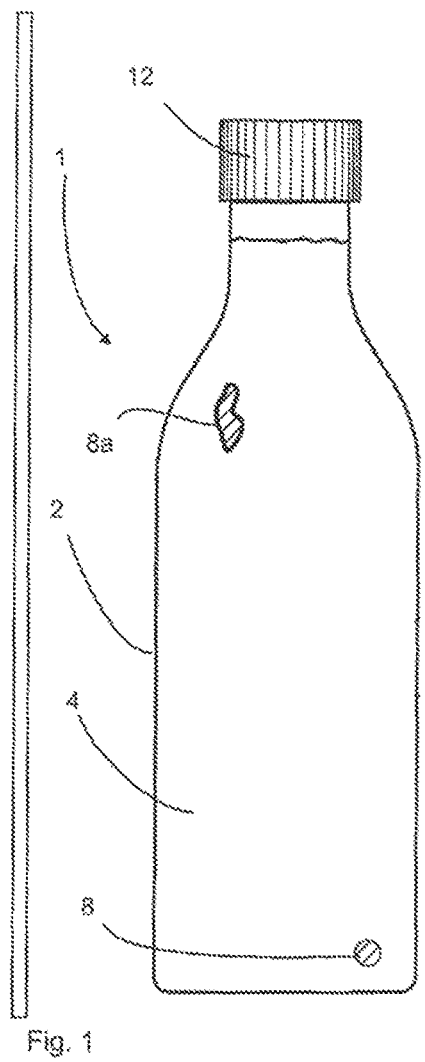
FIG. 1 shows a representation of a container.

FIG. 1 shows a schematic representation of a container 1 according to embodiments of the invention. In this case this container has a circumferential main body 2 as well as a base. A liquid 4 is disposed within the container.

Furthermore the container has a closure 12, such as a screw cap in this case, which closes the container in a liquid-tight manner.

A deliberately introduced foreign body 8 is located within the container or the liquid respectively. This is illustrated here as circular, but it may also have other geometric configurations. In addition it would also be possible to dispose a further foreign body 8a on an inner wall of the container. In this way those inspection processes which react to defects on or in the wall of the container can also be controlled. In addition defects could also be applied in a targeted manner, for example on the main body of the container, such as for example scratches, material irregularities and the like. It would also be possible for a plurality of different foreign bodies to be disposed in the container, in order to test different characteristics of an inspection machine 20 in a targeted manner. In this case it would be possible for these foreign bodies to react differently to movements of the container, such as for example rotations of the container about its longitudinal axis. These foreign bodies can also be made from different materials.

Figure 2:
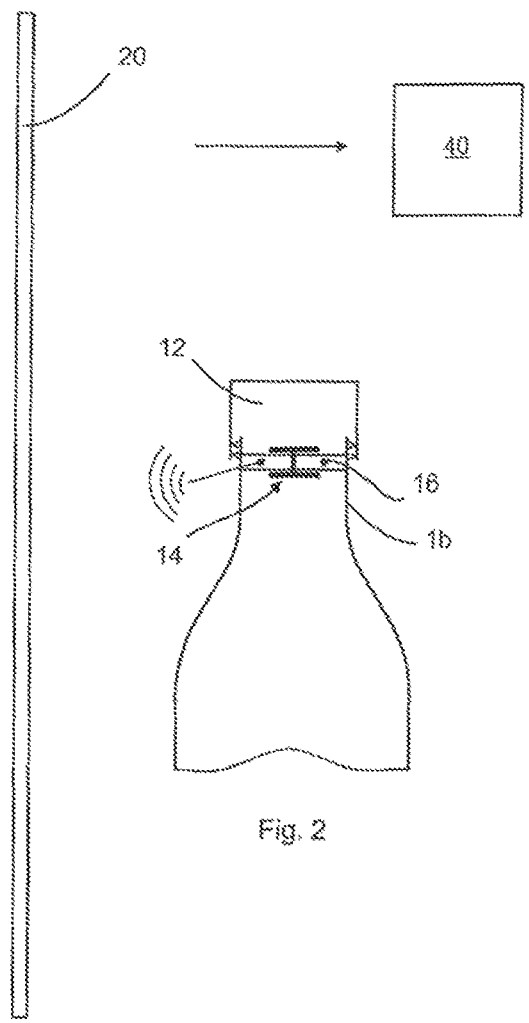
FIG. 2 shows a view of a detail of the container according to FIG. 1.

FIG. 2 shows a detail view of an upper region of the container 1. In this case it can be seen that the container has a second closure 14 which is disposed in a neck region 1b of the container. This second closure means may be a clamping member which, as is indicated in FIG. 2, expands in the direction of the mouth or the inner wall of the mouth respectively and thus likewise securely closes the container. The reference numeral 16 identifies quite schematically a transmitting device which for example can transmit a signal which identifies the container 1. In this case it may for example be an RFID tag or the like or in particular a transmitting device which is activated by an external power source. In this way this element can be activated for example in a machine disposed downstream and can transmit a signal by which the test container which has undesirably entered the output stream of containers is separated out again.

Figure 3:
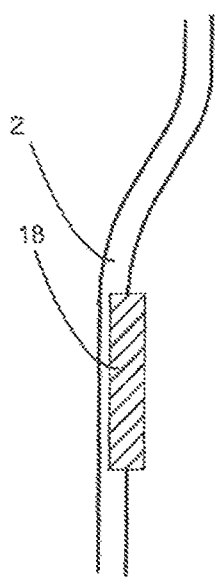
FIG. 3 shows a representation of a wall section of the container.

FIG. 3 shows a detail of the main body 2 or the wall region thereof respectively. It will be recognised that here an element 18 is introduced in the wall. As mentioned above, this element can in turn serve for testing inspection devices. In addition, however, this element 18 may also be an information carrier which for example has a marking or by means of which a marking or an information can be read respectively which unambiguously identifies the test container.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

LIST OF REFERENCE NUMERALS 1 container
1b neck region
2 main body
4 liquid
8 foreign bodies
8a further foreign body
12 closure
14 second closure
16 transmitting device
18 element

The invention claimed is:

1. A test container wherein the test container has a container fully filled with a liquid, said test container having a main body in which the liquid is disposed, wherein the liquid has at least one substance with a germ-killing action, said test container having a mouth via which the liquid is able to be introduced into the container, with a first closure by which the container is closed, wherein a foreign body is disposed in the container and which can be detected during inspection, wherein the container and/or the liquid disposed therein has a test element which can be detected by a user and/or a detection device in order to distinguish the test container from another container, wherein the liquid prevents the multiplication of germs for a long period of time.

2. Test container according to claim 1, wherein the liquid is similar in appearance and index of refraction to a product actually to be used.

3. Test container according to claim 1, wherein the liquid, in particular as a replacement for beer, is a denatured, coloured, high-percentage alcohol solution.

4. Test container according to claim 1, wherein the test container is a test container produced at least partially under sterile conditions.

5. Test container according to claim 1, wherein the liquid in the container has been introduced under sterile conditions and/or also a closure of the container has been manufactured and attached to the container under sterile conditions.

6. Test container according to claim 1, wherein the container has been subjected to radiation which penetrates into the medium used for disinfection or for sterilisation.

7. Test container according to claim 1, wherein the test container is a plastic container or a glass container.

8. Test container according to claim 1, wherein a further substance is located in the liquid, making it possible to differentiate the container on the basis of a smell of the liquid.

9. Test container according to claim 1, wherein the further substance is selected from a group of substances containing acetone, raw pyridine, crystal violet, fusel oil, isopropyl alcohol, methyl ethyl ketone, methyl isopropylene ketone, ethyl sec-amyl ketone, wood alcohol, rock oil, methanol, thiophene, mixtures of these substances.

10. Test container according to claim 1, wherein several foreign bodies with physical characteristics which differ from one another are disposed in the container.

11. Test container according to claim 1, wherein the foreign body is fixed relative to the container.

12. Test container according to claim 1, wherein the test container has an identification element which can be recognised by a machine.

13. Test container according to claim 1, wherein the container has a second closure which closes the container in addition to the first closure.

14. Test container according to claim 13, wherein the second closure is disposed inside a mouth region of the test container.

15. A test container fully filled with a liquid, said test container having a main body in which the liquid is disposed, wherein the liquid has at least one substance with a germ-killing action, said test container having a mouth via which the liquid is able to be introduced into the container, with a first closure by which the container is closed, wherein a foreign body is disposed in the test container and which can be detected during inspection, wherein the container and/or the liquid disposed therein has a test element which can be detected by a user and/or a detection device in order to distinguish the test container from another container of the category to be inspected, wherein the liquid prevents the multiplication of germs for a long period of time, wherein the test container has been subjected to a heat treatment just below the boiling point for a few hours, which effectively slows down the multiplication of germs.

* * * * *